United States Patent [19]

Sekmakas et al.

[11] Patent Number: 4,617,364

[45] Date of Patent: Oct. 14, 1986

[54] WET ADHESION PROMOTERS FOR EMULSION POLYMERS

[75] Inventors: Kazys Sekmakas, Palatine; Raj Shah, Schaumburg, both of Ill.

[73] Assignee: DeSoto, Inc., Des Plaines, Ill.

[21] Appl. No.: 448,254

[22] Filed: Dec. 9, 1982

[51] Int. Cl.[4] .................. C07D 209/56; C07D 239/03; C07D 403/00; C08F 218/14

[52] U.S. Cl. ..................................... 526/263; 544/296; 544/316; 544/318; 548/318; 548/320

[58] Field of Search ....................... 544/316, 318, 296; 548/318, 320; 526/263

[56] References Cited

U.S. PATENT DOCUMENTS

| | | | |
|---|---|---|---|
| 2,980,652 | 4/1961 | Melamed et al. | 526/263 |
| 3,356,653 | 12/1967 | Sekmakas | 548/320 |
| 3,356,654 | 12/1967 | Sekmakas | 526/263 |
| 4,319,032 | 3/1982 | Sandri et al. | 544/316 |
| 4,448,816 | 5/1984 | Barsa et al. | 548/320 |

*Primary Examiner*—Harry Wong, Jr.
*Attorney, Agent, or Firm*—Dressler, Goldsmith, Shore, Sutker & Milnamow, Ltd.

[57] ABSTRACT

Monoethylenically unsaturated copolymerizable monomers are disclosed which improve the adhesion of copolymers (especially those produced by aqueous emulsion copolymerization to provide latex paint). These monomers are the reaction product of one equivalent of a monoethylenically unsaturated compound which resists homopolymerization and which carries a single isocyanate-reactive hydrogen atom, such as 2-hydroxypropyl monobutyl maleate, one mole of an organic polyisocyanate, such as 2,4-toluene diisocyanate, and sufficient alkyl alkylene urea carrying a single isocyanate-reactive hydrogen atom on the alkyl group, such as 2-hydroxyethyl ethylene urea, to consume the remaining isocyanate functionality on the polyisocyanate. An improved method of producing these monomers from a mixture of all three reactants is also disclosed.

13 Claims, No Drawings

WET ADHESION PROMOTERS FOR EMULSION POLYMERS

DESCRIPTION

1. Technical Field

This invention relates to monoethylenically unsaturated copolymerizable monomers which enhance the adhesion of emulsion copolymer latices to an underlying substrate, to the production of such monomers, and to copolymers containing the same.

2. Background Art

The emulsion copolymerization of monoethylenically unsaturated monomers to produce latex emulsions for paints is well known. It is also known to include a small proportion of a monoethylenically unsaturated amine-functional monomer in the monomers which are copolymerized in order to improve the adhesion (both wet and dry) of the latex paint to the substrate which is painted. The objective is to provide the greatest improvement in adhesion in the simplest and most effective manner, the cost being a material factor in achieving this objective.

The prior efforts in this direction are illustrated by U.S. Pat. No. 3,356,653 to K. Sekmakas, but there are many other patents which are concerned, in one way or another, with the same problem.

A recent patent of interest is U.S. Pat. No. 4,319,032 to J. M. Sandri et al. in which the adhesion-promoting monomer is produced by the reaction of an omega aminoalkyl alkylene urea, such as 2-aminoethyl ethylene urea, with an unsaturated glycidyl ether or ester, such as allyl glycidyl ether. It is desired to avoid the use of glycidyl compounds while achieving superior adhesion in a practical fashion, and to do so while retaining the use of an alkyl alkylene urea compound which provides a convenient and economical starting reactant.

DISCLOSURE OF INVENTION

In accordance with this invention, a monoethylenically unsaturated copolymerizable monomer having the capacity to improve the adhesion of copolymers containing from 0.1% to 10% thereof, is the reaction product of one equivalent of a monoethylenically unsaturated compound which resists homopolymerization and which carries a single isocyanate-reactive hydrogen atom, one mol of an organic polyisocyanate, and sufficient alkyl alkylene urea carrying a single isocyanate-reactive hydrogen atom on the alkyl group to consume the remaining isocyanate functionality on the polyisocyanate. It is particularly preferred that the isocyanate-reactive hydrogen atom be supplied by the hydroxy group.

While the specific procedure used may vary (the polyisocyanate can be reacted first with either of the other reactants and then with the other, or with both at the same time as detailed hereinafter), the reaction product has the following formula:

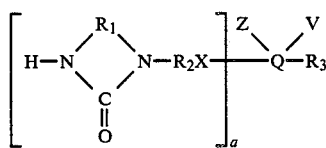

in which $R_1$ is alkylene having 2 or 3 carbon atoms, preferably 2 or 3;

$R_2$ is alkylene having 2 to 10 carbon atoms;

X is a radical which initially carried Z, such as

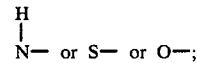

Z is an isocyanate-reactive hydrogen atom initially carried by $R_2X$;

a is an integer from 1 to 5, such as 1 or 2, to consume all the isocyanate groups on the polyisocyanate noted hereinafter other than the one consumed by $R_3$;

Q is an organic aliphatic or aromatic polyisocyanate carrying $a+1$ isocyanate groups;

V is an isocyanate-reactive hydrogen atom initially carried by $R_3$; and $R_3$ is the residue of a monohydroxy $C_1$-$C_{12}$ alkyl maleate or fumarate which is connected to Q via its hydroxy group; and X and $R_3$ are connected to Q via the isocyanate groups therein and Z and V are carried by the nitrogen atoms in said isocyanate groups.

In preferred practice, $R_3$ is a derivative of maleic or fumaric acid, most preferably a derivative of monoalkyl maleate or fumarate.

In accordance with the preferred practice of the invention, the alkyl alkylene urea is 2-hydroxyethyl ethylene urea which provides a primary hydroxyl group, and the monoethylenically unsaturated compound is a derivative of monoalkyl maleate or fumarate, such as hydroxy propyl monobutyl maleate, which provides a secondary hydroxyl group. Allyl alcohol and 2-hydroxypropyl ethylene area will further illustrate materials which may be used. The polyisocyanate may be either aliphatic or aromatic, but aliphatic polyisocyanates are preferred. It is also preferred to employ tri-isocyanates, because these provide the capacity to combine two alkylene urea groups with a single ethylenically unsaturated group.

Referring more particularly to he polyisocyanates which can be used, the several isocyanate groups may possess the same order of reactivity, as in 1,6-hexane diisocyanate, and the two other reactants can be reacted with these isocyanate groups, one at a time. Then, one can purify to obtain the desired monoethylenic derivative. While this is possible, it is better to employ an organic polyisocyanate which contains one isocyanate group which is more or less reactive than the other isocyanate groups. These are illustrated by isophorone diisocyanate, 2,4-toluene diisocyanate, and the trimer formed by reacting three moles of an aliphatic diisocyanate, such as 1,6-hexane diisocyanate, with one mole of water. 2,4,6-toluene triisocyanate is also useful. Then, one can first react one of the two other reactants with the more reactive isocyanate group and then bring in the second other reactant with the other isocyanate groups which are less reactive. This is a conventional procedure which is easily used herein in known manner, but it is preferred to have all the reactants together and to carry out the reaction in two stages, as will be described, for this is simpler and more economical.

In this improved process, the organic polyisocyanate including at least one isocyanate group which is more or less reactive than the others is added slowly to a mixture of the other two components in which the isocyanate-reactive hydrogen atom of the monoethylenically unsaturated compound is more or less reactive than the isocyanate-reactive hydrogen atom of the alkylene urea derivative. The polyisocyanate is preferably selected to include one isocyanate group which is less reactive than the others, and the proportion of the alkylene urea derivative is stoichiometrically related to the more reactive isocyanate groups in the polyisocyanate. On the other hand, if the polyisocyanate includes one more reactive isocyanate group, as in 2,4,6-toluene triisocyanate, the proportion of the alkylene urea derivative is stoichiometric with respect to the less reactive isocyanate groups in the polyisocyanate. In this way, and especially when one uses a polyisocyanate having one less reactive isocyanate group with an alkylene urea derivative containing a primary hydroxy group, such as hydroxyethyl ethylene urea, and a maleate or fumarate derivative containing a secondary hydroxy group, such as 2-hydroxypropyl monobutyl maleate, then a pure monoethylenically unsaturated product is obtained even though the customary two-stage reaction is not performed.

In practice, sufficient amounts of a solvent, such as methyl ethyl ketone and/or butanol, is used in the production of the monomers to provide a fluid liquid mixture. Temperatures up to about 60° C., preferably from 40° C. to 50° C., can be used to react the more reactive isocyanate group with a primary hydroxyl group or with one hydrogen atom of a primary amine, but higher temperatures, up to about 80° C., are useful to react a less reactive isocyanate group with secondary hydroxyl or carboxyl. Catalysts for the isocyanate reaction, such as dibutyl tin dilaurate, are well known and are normally present to aid the reaction. The choice of catalyst and the selection of the active hydrogen atom with which reaction will be had will vary the temperature which should be employed somewhat, but this is easily adjusted as known to the art.

The monomers of this invention may be incorporated in small proportion, preferably from 0.5% to 5%, by addition copolymerization into polymers which consist essentially of copolymerized monoethylenically unsaturated monomers. While the polymerization process may be of diverse types, such as solvent solution polymerization, it is preferred that the copolymer be formed by aqueous emulsion copolymerization. In this way the copolymers are provided in the form of an aqueous latex which is stabilized by the presence of surfactants, as illustrated in the patents noted previously. Latex paints which coalesce at room temperature are particularly desired, and for this purpose the monmers of the copolymer and their proportions are selected to provide the copolymer with a $T_g$ (glass transition temperature) in the range of $-20°$ C. to $+20°$ C., preferably in the range of $-10°$ C. to $+10°$ C.

In typical commercial practice, at least about 90% of said copolymerized monomers are selected from $C_1$–$C_8$ alkyl esters of acrylic and methacrylic acids, such as ethyl acrylate, butyl acrylate and methyl methacrylate, vinyl acetate, and ethylene.

Adhesion is of special importance in interior latex paints of semi-glass character which can be expected to be applied over glossy oil-based paints which are difficult to adhere to. The examples will therefore emphasize copolymers of vinyl acetate and butyl acrylate which are frequently used in such semi-gloss paints.

Traces of residual isocyanate functionality which may remain at the end of the reaction are removed by reaction with an alcohol, and as butanol, or other solvent-type alcohol.

The invention is illustrated by the examples which follow:

EXAMPLE 1

Charge to a reactor equipped with a reflux condenser 130 grams (1 Equiv. OH) of 2-hydroxyethyl ethylene urea, 230 grams (1 Equiv. OH) of 2-hydroxypropyl-mono-n-butyl maleate and 180 grams of methyl ethyl ketons. Set the reflux condenser and heat the mixture to 50° C. with agitation. Add slowly (over a 45-minute period) 174 grams (2 Equiv. NCO) of 2,4-toluene diisocyanate. Hold for 2 hours at 50° C., then heat to 70° C. and hold for one hour. Add 50 grams of butanol and hold 1 hour. Cool to 30° C. and store. A solution product was obtained containing 69.8% non-volatile solids.

EXAMPLE 2

Charge to a reactor equipped with a reflux condenser 260 grams (2 Equiv. OH) 2-hydroxyethyl ethylene urea, 230 (1 Equiv. OH) 2-hydroxypropyl-mono-n-butyl maleate and 375 grams methyl ethyl ketone. Set the reflux condenser and heat the mixture to 50° C. with agitation using a nitrogen sparge. Add slowly (over a 1-hour period) 760 grams (3 Equiv. NCO) [See Note 1 for a description of the aliphatic triisocyanate used.] Hold for 2 hours at 50° C. Heat to 70° C. and hold for one hour. Add 100 grams butanol and hold for 30 minutes at 70° C. Cool to 30° C. A solution product was obtained containing 63.5% non-volatile solids.

Note 1

The aliphatic triisocyanate is the reaction product of 3 moles of 1,6-hexane diisocyanate with one mole of water, the reaction liberating carbon dioxide. One of the three isocyanate groups in this triisocyanate is less reactive than the other two. The Mobay product Desmodur N may be used. In this instance it is used in a 75% solution which would be designated N-75. The solvent is an equiv. weight mixture of 2-ethoxyethanol acetate and xylol.

EXAMPLE 3

Charge to a reactor equipped with a reflux condenser 130 grams (1 Equiv. OH) 2-hydroxyethyl ethylene urea, 230 grams (1 Equiv. OH) 2-hydroxypropyl mono-n-butyl maleate and 180 grams methyl ethyl ketone. Set the reflux condenser and heat the mixture to 50° C. with agitation. Add slowly (over a 45-minute period) 222 grams (2 Equiv. NCO) of isophorone diisocyanate. Hold for 2 hours at 50° C., then heat to 70° C. and hold for one hour. Add 50 grams butanol and 30 grams methyl ethyl ketone. Hold for 30 minutes at 70° C., Cool to 30° C. and store. A solution product was obtained containing 69.0% non-volatile solids.

When the monomers of this invention are added to the monomer mixture which is copolymerized in aqueous emulsion (as illustrated in U.S. Pat. No. 3,356,653), the wet adhesion properties of paints made from the resulting latices is greatly improved. This has been evaluated in a series of latex paints which have been pigmented in standard fashion to provide a semi-gloss paint. In each instance, the latex was based on an aqueous emulsion copolymer containing from 54% to 55% of non-volatile solids and having a pH of about 7.0 and which is made from a monomer mixture containing 84 parts vinyl acetate, 14 parts n-butyl acrylate and 2.0 parts of the monomer providing improved wet adhesion.

The results are tabulated in the tables presented hereinafter in which adhesion of the cured film to a glossy oil-base paint substrate is measured in two fashions, namely: by the Wet Slide and Wet Peel Tests. These tests are standard industry tests in which the coating is cut in a line, immersed in water and then an effort is made to remove as much of it as possible either by sliding abrasion or by an effort to peel it away with the fingernails. The test results are reported on a scale of 0 to 5, 0 denoting complete removal of the film and 5 indicating that no film has been removed. Two controls are used in the tabulation. The first control employs the ester of 2-hydroxy ethyl ethylene urea with maleic anhydride which is then esterified with 1,2-propylene oxide in accordance with the teachings of U.S. Pat. No. 3,356,653. The second control is identified as a commercial emulsion which is presently being used in commerce for semi-gloss paints of the character under consideration.

TABLE I

| | WET ADHESION TEST | | | | |
|---|---|---|---|---|---|
| Emulsion Tested | Control No. 1 | Commercial Emulsion | Ex. 1 | Ex. 2 | Ex. 3 |
| Wet Slide | 3 | 0 | 2 | 5 | 3 |
| Wet Peel | 3 | 0 | 2 | 5 | 3 |

The above tests were repeated using a different semi-gloss paint formulation to obtain the following results.

TABLE II

| | WET ADHESION TEST | | | | |
|---|---|---|---|---|---|
| Emulsion Tested | Control No. 1 | Commercial Emulsion | Ex. 1 | Ex. 2 | Ex. 3 |
| Wet Slide | 2 | 1 | 2 | 4 | 2 |
| Wet Peel | 3 | 1 | 3 | 4 | 2 |

As can be seen from the tabulated data, all of the adhesion promoters provide a significant improvement over the commercial control. It will further be seen that the monomers of this invention provide results which are at least approximately as good as those obtainable in the prior art referred to. Results will vary, as shown, depending upon the specific paint formulation, and this raises the prospect that the monomers of this invention will be advantageous in sme formulations. The tabulated data also shows an outstanding improvement when a triisocyanate is used to provide a monomer product having two ethylene urea derivatives joined to a single monoethylenically unsaturated group.

As a matter of interest, Examples 1, 2 and 3 have been repeated using one equivalent of 2-hydroxy ethyl methacrylate in place of one equivalent of 2-hydroxypropyl-monobutyl maleate. The reaction mixture gelled in each instance to form an insoluble and useless product. In the repeat of Example 2, gellation occurred before addition of the triisocyanate was complete. The tendency of the monomer known to form homopolymers to this while the reaction with isocyanate functionality is in progress in the presence of the amine-functional alkylene urea simply is to strong to allow useful products to be produced.

What is claimed is:

1. A monoethylenically unsaturated copolymerizable monomer having the formula

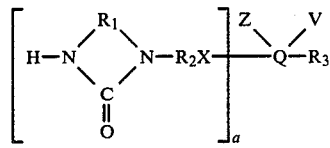

in which
   $R_1$ is alkylene having 2 to 3 carbon atoms;
   $R_2$ is alkylene having 2 to 10 carbon atoms;
   X is a radical selected from NH—, S—, and O— which initially carried Z;
   Z is an isocyanate-reactive hydrogen atom initially carried by $R_2X$;
   a is an integer from 1 to 5 to consume all the isocyanate groups on the polyisocyanate noted hereinafter other than the one consumed by $R_3$;
   Q is an organic aliphatic or aromatic polyisocyanate carrying a+1 isocyanate groups;
   V is an isocyanate-reactive hydrogen atom initially carried by $R_3$;
   $R_3$ is the residue of a monohydroxy $C_1$–$C_{12}$ alkyl maleate or fumarate which is connected to Q via its hydroxy group; and
   X and $R_3$ are connected to Q via the isocyanate groups therein and Z and V are carried by the nitrogen atoms in said isocyanate groups.

2. A monomer as recited in claim 1 in which X is O.

3. A monomer as recited in claim 1 in which $R_1$ contains 2 carbon atoms.

4. A monomer as recited in claim 1 in which $R_2$ contains 2 carbon atoms.

5. A monomer as defined in claim 1 in wnhich X is O and $R_1$ and $R_2$ each contain 2 carbon atoms.

6. A monomer as recited in claim 1 in which a is 1.

7. A monomer as recited in claim 5 in which a is 1.

8. A monomer as recited in claim 1 in wnhich $R_3$ is the residue of hydroxy propyl mono $C_2$–$C_4$ alkyl maleate.

9. A copolymer consisting essentially of copolymerized monoethylenically unsaturated monomers including from 0.1% to 10% of the monomer recited in claim 1.

10. A copolymer as recited in claim 9 in which said copolymer is formed by aqueous emulsion copolymerization.

11. A copolymer as recited in claim 10 in which said copolymer has a $T_g$ in the range of −20° C. to +20° C.

12. A copolymer as recited in claim 11 in which at least about 90% of said copolymerized monomers are selected from the group consisting of $C_1$–$C_8$ alkyl esters of acrylic and methacrylic acids, vinyl acetate, and ethylene.

13. A copolymer as recited in claim 12 in which said copolymer has a $T_g$ in the range of −10° C. to +10° C.

* * * * *